United States Patent [19]

Corbett et al.

[11] 4,438,036
[45] Mar. 20, 1984

[54] β-LACTAM ANTIBIOTICS THEIR PREPARATION AND THEIR USE

[75] Inventors: David F. Corbett, Reigate; Robert Southgate, Warnham; Steven Coulton, Cranleigh, all of England

[73] Assignee: Beecham Group Limited, England

[21] Appl. No.: 310,491

[22] Filed: Oct. 13, 1981

[30] Foreign Application Priority Data

Oct. 25, 1980 [GB] United Kingdom ................. 8034453

[51] Int. Cl.$^3$ ............................................ C07D 487/04
[52] U.S. Cl. .............................. 260/245.2 T; 424/274; 424/269; 424/270; 424/273 R; 424/114; 544/3.6

[58] Field of Search ................................. 260/295 LT

[56] References Cited

FOREIGN PATENT DOCUMENTS 1628 5/1979 European Pat. Off. ........ 260/245.27

Primary Examiner—Mary C. Lee
Attorney, Agent, or Firm—Jacobs & Jacobs

[57] ABSTRACT

The present invention provides a process for inversion of the absolute stereochemistry at the α-carbon atom of a C-6 substituent of a bicyclic carbapenem antibiotic via a phosphorus - azodicarboxylate mediated reaction. Novel azides, amines and formates are described as useful intermediates and as antibacterial agents.

5 Claims, No Drawings

β-LACTAM ANTIBIOTICS THEIR PREPARATION AND THEIR USE

This invention relates to substituted carbapenems, to processes for their preparation and their use.

European Patent Application Publication Nos. 0001627 and 0001628 discloses a group of synthetic antibacterial agents of the formula (I):

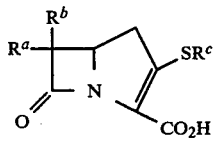

wherein $R^a$, $R^b$, $R^c$ may be selected from a wide range of substituents. However all compounds described in that specification were racemic and could only be prepared by a lengthy synthetic sequence. A new process has been discovered that enables new antibacterial agents to be prepared by a relatively short reaction sequence and these new antibacterial agents are produced as a single optical isomer.

This present invention provides a process for inverting the absolute stereochemistry at the C-8 position (that is, the α-carbon atom of the C-6 substituent).

Accordingly this invention provides a process for the preparation of a compound of the formula (II):

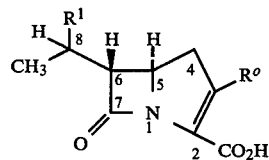

and salts and esters thereof wherein $R^1$ is an azido, amino or hydroxy group, or is a group of the sub-formula (a):

 (a)

wherein $R^3$ is a hydrogen atom or a $C_{1-6}$ alkyl, aryl or aryl $C_{1-6}$ alkyl group; and $R^o$ is hydrogen or an organic group; which process comprises the reaction of an ester of a compound of the formula (III):

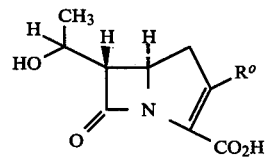

wherein the stereochemistry of C-8 is inverted compared to that at C-8 of the compound of the formula (II), with (a) a compound of the formula (IV):

 (IV)

wherein $R^4$ is azido or a group of the sub-formula (a) $OCOR^3$, wherein $R^3$ is hydrogen, $C_{1-6}$ alkyl, aryl or aryl $C_{1-6}$ alkyl;

(b) a compound of the formula (V):

 (V)

wherein $R^5$ and $R^6$ are independently $C_{1-6}$ alkyl, aryl $C_{1-6}$ alkyl or aryl; and (c) a compound of the formula (VI):

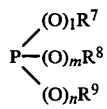 (VI)

wherein l, m and n are independently zero or one and $R^7$, $R^8$ and $R^9$ are independently a $C_{1-6}$ alkyl, aryl $C_{1-6}$ alkyl or aryl group; and thereafter if necessary:

(i) converting a compound of the formula (II) wherein $R^1$ is an azido group to a compound of the formula (II) wherein $R^1$ is an amino group;

(ii) converting a compound of the formula (II) wherein $R^1$ is a group of the sub-formula (a) to a compound of the formula (II) wherein $R^1$ is a hydroxy group.

If the stereochemical configuration at C-8 in the compound of the formula (III) is R, then the stereochemical configuration at C-8 in the product of the formula (II) is S. If the stereochemical configuration at C-8 in the compound of the formula (III) is S, then the stereochemical configuration at C-8 in the product of the formula (II) is R.

Suitable compounds of the formula (IV) are hydrazoic acid and formic acid.

Suitable compounds of the formula (V) include those wherein $R^5$ and $R^6$ are independently selected from methyl, ethyl, propyl, butyl, phenyl, and benzyl. It is generally convenient that $R^5$ and $R^6$ each represent the same moiety.

Particularly suitable compounds of the formula (V) include those wherein $R^5$ and $R^6$ each represent an ethyl, t-butyl group or isopropyl group.

Suitable compounds of the formula (VI) include those wherein the $R^7$, $R^8$ and $R^9$ groups are selected from methyl, ethyl, n-propyl, n-butyl, benzyl, phenyl and methoxyphenyl groups. It is generally convenient that $R^7$, $R^8$ and $R^9$ each represent the same moiety.

Favoured compounds of the formula (VI) include tri-aryl phosphines and tri-alkyl phosphites. Particularly suitable compounds of the formula (VI) include triphenylphosphine, trimethylphosphite and triethylphosphite, of these triphenylphosphine is preferred.

Suitably $R^o$ is an optionally substituted hydrocarbon group of 1 to 20 carbon atoms.

More suitably $R^o$ is an etherified or acylated mercapto group, the sulphur atom of which is optionally oxidised so that the moiety may be in the form of a sulphide or sulphoxide. Most suitably $R^o$ is a group $S(O)_xR^2$ wherein x is zero or one, and $R^2$ is $C_{1-6}$ alkyl, $C_{2-6}$ alkenyl, $C_{2-6}$ alkynyl, aryl ($C_{1-6}$) alkyl, $C_{1-6}$ alkanoyl, aryl $C_{1-6}$ alkanoyl, aryloxy ($C_{1-6}$) alkanoyl, arylcarbonyl, aryl or a heterocyclyl, heterocyclyl ($C_{1-6}$) alkyl, heteroaryl ($C_{1-6}$) alkyl or heteroaryl group wherein the hetero atom or hetero atoms in the above named heteroaryl and/or heterocyclyl moieties are selected from 1-4 oxygen, nitrogen or sulphur atoms; any of such $R^2$ groups being optionally substituted. Preferably x is zero.

When $R^2$ is a $C_{1-6}$alkyl group suitable substituents include amino, di-($C_{1-6}$)alkylamino, $C_{1-6}$ alkylamino, acylamino, hydroxy, $C_{1-6}$ alkanoyloxy, $C_{1-6}$ alkoxy, benzoyl, $C_{1-6}$ alkanoyl or carboxy or an ester or salt thereof.

More suitably such alkyl groups contain up to 4 carbon atoms, for example $R^2$ aptly may be methyl, ethyl, propyl, butyl, aminomethyl, aminoethyl, aminopropyl, aminobutyl, hydroxyethyl, hydroxypropyl, hydroxybutyl, methoxymethyl, methoxyethyl, ethoxymethyl, ethoxyethyl, propoxypropyl, methoxypropyl, methoxybutyl, acetoxymethyl, acetoxyethyl, propionoxymethyl, propionoxyethyl, phenacyl, acetylmethyl, acetylethyl, propionylmethyl, propionylethyl, carboxymethyl or pharmaceutically acceptable salt thereof, methoxycarbonylmethyl, ethoxycarbonylmethyl, methoxycarbonylethyl, methoxycarbonylpropyl, methoxycarbonylbutyl, ethoxycarbonylethyl, carboxyethyl or pharmaceutically acceptable salt thereof, carboxypropyl or pharmaceutically acceptable salt thereof, carboxybutyl or pharmaceutically acceptable salt thereof, acetamidoethyl and propionamidoethyl. Of these values methyl, ethyl, propyl, butyl, 2-aminoethyl and acetamidoethyl are preferred.

When $R^2$ is a $C_{2-6}$ alkenyl group wherein the double bond is not present on the carbon adjacent to the sulphur atom, suitable substituents include carboxy or an ester or pharmaceutically acceptable salt thereof, or hydroxy or $C_{1-6}$ alkoxy.

When $R^2$ is a $C_{2-6}$ alkenyl group wherein the double bond is present on the carbon adjacent to the sulphur atom, suitable substituents include carboxy or an ester or pharmaceutically acceptable salt thereof.

More suitably $R^2$ is propenyl, butenyl and $CH=CH-CO_2H$ or a pharmaceutically salt or ester thereof, for example the sodium or potassium salt or the methyl, ethyl, propyl, aminoethyl, aminopropyl, benzyl or p-nitrobenzyl ester.

In another aspect preferred values for $R^2$ include the acetamidoethenyl and propionamidoethenyl groups.

Suitable aryl, heteroaryl and heterocyclyl groups for use in the substituent $R^2$ include phenyl, naphthyl, pyrrolyl, furyl, tetrazolyl, thienyl, indolyl, thionaphthyl, benzofuryl, imidazolyl, thiazolyl, or any of such groups substituted by one or more groups selected from $C_{1-3}$ alkyl, phenyl, nitro and amino; or a phenyl group optionally substituted by halogen atom or a $C_{1-3}$ alkoxy, nitro or acetamido group.

When $R^2$ is an aryl $C_{1-6}$ alkyl, heteroaryl $C_{1-6}$ alkyl or heterocyclyl $C_{1-6}$ aryl group, more suitably the alkyl moiety is a methylene or ethylene divalent radical. Suitable examples of such aryl and heteroaryl moieties are phenyl optionally substituted by one or more substituents selected from a halogen atom or a $C_{1-3}$ alkoxy, nitro or acetamido group; pyrrolyl optionally substituted by a phenyl or $C_{1-3}$ alkyl group; thienyl optionally substituted by a phenyl or $C_{1-3}$ alkyl group; furyl optionally substituted by a phenyl or $C_{1-3}$ alkyl group; tetrazolyl optionally substituted by phenyl or a $C_{1-3}$ alkyl group; imidazolyl optionally substituted by one or more groups; selected from phenyl, nitro, amino, $C_{1-3}$ alkyl; and thiazolyl optionally substituted by one or more groups selected from phenyl, nitro, amino and $C_{1-3}$ alkyl.

More suitably $R^2$ is a benzyl, bromobenzyl, chlorobenzyl, fluorobenzyl, methoxybenzyl, nitrobenzyl, acetamidobenzyl, thiazolylmethyl, aminothiazolylmethyl, nitrothiazolylmethyl or phenylthiazolylmethyl group.

Suitably also $R^2$ is phenethyl, pyrrolylethyl or optionally substituted tetrazolylethyl or imidazolylethyl. In a suitable aspect the imidazolyl ring may be substituted at the C-2 position (that is the carbon atom α to the two nitrogen atoms) by a $C_{1-3}$ alkyl or phenyl group. In another aspect the imidazolyl ring may be further substituted at the C-4 position or the C-5 position by a $C_{1-3}$ alkyl, phenyl, nitro or amino groups; preferably such substituents are on the C-4 position and the C-5 position is unsubstituted; alternatively such substituents are on the C-5 position and the C-4 position is substituted.

In a further aspect $R^2$ is a $C_{1-6}$ alkanoyl, aralkanoyl, aroxyalkanoyl or aroyl group, for example acetyl, phenylacetyl, phenoxyacetyl or benzoyl. Of these acetyl is preferred.

Suitably $R^2$ is phenyl optionally substituted by a halogen atom or a $C_{1-3}$ alkyl, $C_{1-3}$ alkoxy, nitro or acetamido group. Suitably $R^2$ is a 5- or 6-membered aromatic heterocyclic group containing 1 or 2 nitrogen atoms such as the pyridyl, pyrimidyl, pyrrolyl and imidazolyl ring systems, for example 2-pyridyl, 3-pyridyl, 4-pyridyl, 2-pyrimidinyl, 4-pyrimidinyl, 5-pyrimidinyl, 2-pyrrolyl, 3-pyrrolyl, 2-imidazolyl and 4-imidazolyl. Of these the pyridyl and pyrimidinyl ring systems are favoured, the pyrimidinyl ring being preferred and in particular the 2-pyrimidinyl and 4-pyrimidinyl ring systems. Suitably such aromatic heterocyclic ring systems are optionally substituted by one or more $C_{1-4}$ alkyl or $C_{1-4}$ alkanoyloxy groups.

The compounds of the formula (II) wherein $R^1$ is azido are antibacterially active in their own right but are primarily envisaged as intermediates in the preparation of compounds of the formula (II) wherein $R^1$ is amino.

When the compounds of the formula (II) and salts and esters thereof are intended for use as antibacterial agents, then suitably the compound is in the form of an in-vivo hydrolysable ester or pharmaceutically acceptable salt. Suitable pharmaceutically acceptable salts include those of the alkali and alkaline earth metals, of these the sodium and potassium salts are preferred.

Suitably for use as an intermediate, for example in the preparation of a compound of the formula (II) or a salt thereof, the compound of the formula (II) is provided in the form of a cleavable ester at the C-2 carboxyl. Apt cleavable esters include those cleavable by chemical methods such as hydrogenolysis, hydrolysis, electrolysis or photolysis, and biological methods such as in-vivo hydrolysis and enzymatic hydrolysis.

Suitably the esterifying group is an alkyl, alkenyl, aryl or aralkyl, group which may be substituted if desired. Preferably the alkyl, alkenyl and alkynyl groups and the alkyl portion of the aralkyl group contain up to 6 carbon atoms. Suitable substituents which may be included in the esterifying group include halogen atoms and $C_{1-6}$ alkoxy, $C_{1-6}$ alkanoyl, hydroxy, $C_{1-6}$ acyloxy for example $C_{1-6}$ alkanoyloxy, $C_{1-6}$ alkylamino and di($C_{1-6}$) alkylamino groups.

More suitably the carboxylic acid is esterified by a group of the sub-formula (b), (c), (d), (e), (f) or (g):

(b)

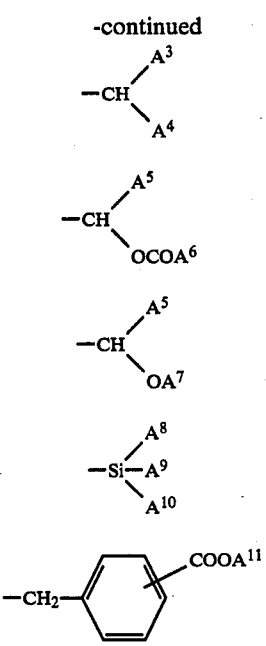

wherein $A^1$ is a hydrogen atom, $C_{1-6}$ alkanoyl or an $C_{1-5}$ alkyl group optionally substituted by $C_{1-7}$ alkoxy or $C_{1-7}$ carboxylic acyloxy, or an alkenyl or alkynyl group of up to 5 carbon atoms; $A^2$ is a hydrogen atom or a methyl group; $A^3$ is a phenyl group or a phenyl group substituted by a fluorine, chlorine or bromine atom or a nitro, $C_{1-3}$ alkyl or $C_{1-3}$ alkoxy group; $A^4$ is a hydrogen atom or a phenyl group or phenyl group substituted by a fluorine, chlorine or bromine atom or a nitro, $C_{1-3}$ alkyl or $C_{1-3}$ alkoxy group; $A^5$ is a hydrogen atom or a methyl group; $A^6$ is a $C_{1-6}$ alkyl, phenyl, phenoxy, phenyl ($C_{1-3}$) alkyl, phenyl ($C_{1-3}$) alkoxy or $C_{1-6}$ alkoxy group or $A^5$ is joined to $A^6$ to form a phthalidyl, dimethylphthalidyl or dimethoxyphthalidyl group; $A^7$ is a $C_{1-4}$ alkyl, phenyl, chlorophenyl or nitrophenyl group; $A^8$ is a $C_{1-4}$ alkyl or phenyl group; $A^9$ is a $C_{1-4}$ alkyl or phenyl group; $A^{10}$ is $C_{1-4}$ alkyl; and $A^{11}$ is $C_{1-4}$ alkyl: or $CHA^1A^2$ is a phenacyl or bromophenacyl group.

Favourably $A^1$ is a hydrogen atom or a methyl, ethyl, vinyl or ethenyl group. Favourably $A^2$ is a hydrogen atom. Favourably $A^3$ is a phenyl, p-bromophenyl, p-methoxyphenyl or p-nitrophenyl group. Favourably $A^4$ is a hydrogen atom. Favourably $A^6$ is a methyl, t-butyl or ethoxy group or is joined to $A^5$. Favourably $A^7$ is a methyl group. Favourably $A^5$ is a hydrogen atom.

Preferred groups of the sub-formula (b) include the methyl, ethyl and acetonyl groups.

Preferred groups of the sub-formula (c) include the benzyl and p-nitrobenzyl groups.

When $A^5$ is hydrogen, suitably $A^6$ is selected from methyl, ethyl, n-propyl, iso-propyl, n-butyl, tert-butyl, phenyl, benzyl, methoxy, ethoxy, n-propyloxy and iso-propyloxy. Preferably $A^6$ is tert-butyl. Preferred groups of the sub-formula (d) include the acetoxymethyl, pivaloyloxymethyl, ethoxycarbonyloxymethyl, phthalidyl, α-ethoxycarbonyloxyethyl and α-acetoxyethyl groups. These esterifying groups are favoured as they tend to form in-vivo hydrolysable esters.

A preferred group of the sub-formula (e) is the methoxymethyl group.

Preferred groups of the sub-formula (f) include the trimethylsilyl, tert-butyldimethylsilyl and tert-butyldiphenylsilyl groups.

A preferred group of the sub-formula (g) is p-methoxycarbonylbenzyl.

Particularly preferred esterifying groups are the p-nitrobenzyl and phthalidyl groups.

The in-vivo hydrolysable nature of the ester may be confirmed by administration to an animal such as a mouse or rat and determination of the presence of a compound of the formula (II) or a salt thereof in the blood or urine of the animal. Alternatively hydrolysis in human blood or serum may be determined.

In general any convenient ester of the compound of the formula (III) may be used in the process of this invention. Suitable esters include those of the subformulae (b)–(g) as hereinbefore specified.

In general it has proved convenient to use one equivalent of the compound of the formula (III), approximately two equivalents of the compounds of the formulae (V) and (VI), and from two to five equivalents of the compound of the formula (IV).

The reaction is performed in an inert organic solvent which should be aprotic and unreactive towards the reagents involved. Suitable solvents include tetrahydrofuran, dioxan, 1,2-dimethoxyethane, benzene, toluene and mixtures of such solvents. Preferably the solvents used are substantially anhydrous. Preferred solvents include tetrahydrofuran, benzene, toluene and mixtures thereof.

The reaction is normally carried out at a non-extreme temperature such as −60° to +100° C., more suitably from about −10° to +50° C. and most conveniently at ambient temperature (approximately +20° C.).

In the process of this invention any amino group present can be conveniently protected in conventional manner, for example as a p-nitrobenzyloxycarbonylamino group. Any hydroxy group present in the ester group or in the substituent $R^o$ should be protected in conventional manner, for example as a p-nitrobenzyloxycarbonyloxy group.

A compound of the formula (II) wherein $R^1$ is an azido group may be converted to a compound of the formula (II) wherein $R^1$ is an amino group by standard reduction methods, such as catalytic hydrogenation, for example using a transition metal catalyst such as palladium suitably palladium on carbon.

A compound of the formula (II) wherein $R^1$ is a group of the sub-formula (a) may be converted to a compound of the formula (II) wherein $R^1$ is a hydroxy group by standard hydrolysis methods, for example using an alkali or alkaline earth metal salt in aqueous solution. Suitable salts include sodium hydroxide, sodium bicarbonate, potassium bicarbonate, sodium carbonate, potassium carbonate and potassium hydroxide. Of these sodium hydroxide is preferred when the C-2 carboxyl group is esterified, and sodium bicarbonate is preferred when the C-2 carboxyl group is salified.

The compounds of the formula (III) may be obtained from natural sources or may be obtained by synthetic methods, see for example the disclosures of European Patent Application Publication Nos. 0001627 and 0024832 and Belgian Patent No. 864,570.

Methods of removing protecting groups, cleaving any ester moiety to a free acid or salt, and converting a free acid or salt to a pharmaceutically acceptable salt or ester are as detailed in the above European Patent Applications which are incorporated herein by reference.

Certain compounds produced by this process are novel and as such form part of this invention.

Accordingly, the present invention provides the compounds of the formula (IX):

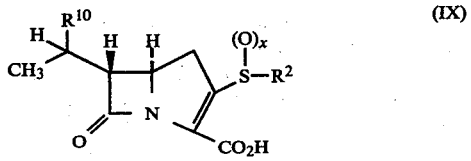

and salts and esters thereof, wherein $R^2$ and x are as herein above defined, and $R^{10}$ is an azido or amino group.

In one aspect $-S(O)_xR^2$ is as hereinabove defined with the proviso that $-S(O)_xR^2$ is not $SCH_2CH_2NH_2$, $SCH_2CH_2N=CHNH_2$, $SCH_2CH_2N=C(CH_3)NH_2$ or $SCH_2CH_2N=C(NH_2)NH_2$. Suitable and apt values for $R^2$ in the compounds of the formula (IX) are as described hereinbefore in relation to the compound of the formula (III). Favourably in the compounds of the formula (IX), x is zero.

The present invention further provides the compounds of the formula (X):

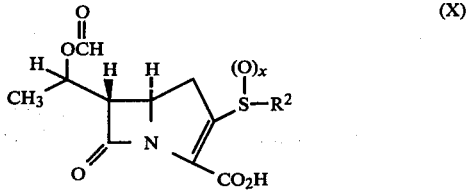

and salts and esters thereof, wherein $R^2$ and x are as hereinabove defined, with the proviso that $-S(O)_xR^2$ is not 2-aminoethylthio. Suitable and apt values for $R^2$ in the compounds of the formula (X) are as described hereinbefore in relation to the compound of the formula (III). Favourably in the compounds of the formula (X), x is zero.

The compounds of the formulae (IX) and (X) and their pharmaceutically acceptable salts and in-vivo hydrolysable esters may be employed in the treatment of bacterial infections such as those due to *Staphylococcus aureus, Escherichia coli* and *Klebsiella aerogenes*. Thus the present invention provides a pharmaceutical composition which comprises a compound of the formulae (IX) or (X) in the form of its pharmaceutically acceptable salt or in-vivo hydrolysable ester and a pharmaceutically acceptable carrier.

The compositions of this invention may be prepared by conventional methods of preparing antibiotic compositions and in conventional manner may be adapted for oral, topical or parenteral administration.

Aptly, the compositions of this invention are in the form of a unit-dose composition adapted for oral administration.

Alternatively the compositions of this invention are in the form of a unit dose composition adapted for administration by injection.

Unit-dose forms according to this invention will normally contain from 50 to 500 mgs of a compound of this invention, for example about 62.5, 100, 125, 150, 200, 250 or 300 mgs. Such compositions may be administered from 1 to 6 times a day or more conveniently 2, 3 or 4 times a day so that the total daily dose for a 70 kg adult is about 200 to 2000 mg, for example about 400, 600, 750, 1000 or 1500 mg.

The compositions of this invention may be used to treat infections in humans and animals, for example infections of the respiratory tract, urinary tract or soft tissues in humans or mastitis in cattle.

The carriers used in the compositions of this invention may include diluents, binders, disintegrants, lubricants, colours, flavouring agents or preservatives in conventional manner. Thus suitable agents include lactose, starch, sucrose, calcium phosphate, sorbitol, polyvinylpyrrolidone, acacia, gelatin, tragacanth, potato starch or polyvinylpolypyrrolidone, magnesium stearate or sodium lauryl sulphate.

Orally administrable forms of the compositions of this invention are most suitably in the form of unit-dose units such as tablets or capsules.

The present invention also provides synergistic pharmaceutical compositions which comprise a pharmaceutical composition as hereinbefore described which also contains a penicillin or a cephalosporin.

Suitable penicillins for inclusion in the compositions of this invention include benzyl penicillin, phenoxymethylpenicillin, ampicillin or a pro-drug therefor, amoxycillin or a pro-drug therefor, carbenicillin or a pro-drug therefor, ticarcillin or a pro-drug therefor, suncillin, sulbenicillin, azlocillin or mezlocillin.

Particularly suitable penicillins for inclusion in orally administrable compositions of this invention include ampicillin and its orally administrable pro-drugs, amoxycillin and its orally administrable pro-drugs and orally administrable pro-drugs of carbenicillin. Thus particularly suitable penicillins include ampicillin anhydrate, ampicillin trihydrate, sodium ampicillin, talampicillin hydrochloride, pivampicillin hydrochloride and bacampicillin hydrochloride; amoxycillin trihydrate, sodium amoxycillin; and the sodium salts of the phenyl and 5-indanyl α-esters of carbenicillin.

A preferred penicillin for inclusion in the orally administrable compositions of this invention is amoxycillin trihydrate. A further preferred penicillin for inclusion in the orally administrable compositions of this invention is ampicillin trihydrate.

Particularly suitable penicillins for inclusion in injectably administrable compositions of this invention include injectable salts such as the sodium salt of ampicillin, amoxycillin, carbenicillin and ticarcillin.

A preferred penicillin for inclusion in the injectably administrable compositions of this invention is sodium amoxycillin. A further preferred penicillin for inclusion in the injectably administrable compositions of this invention is sodium ampicillin.

Particularly suitable cephalosporins for inclusion in the compositions of this invention include cephaloridine, cephalexin, cephradine, cefazolin and cephalothin.

A particularly suitable cephalosporin for inclusion in the orally administrable compositions of this invention is cephalexin.

Particularly suitable cephalosporins for inclusions in the injectably administrable compositions of this invention include cephaloridine, cefazolin and cephradine, generally as their pharmaceutically acceptable salt.

The weight ratio between compound of this invention and penicillin or cephalosporin is generally from 10:1 to 1:10, more usually from 5:1 to 1:5 and normally from 3:1 to 1:3.

The penicillin or cephalosporin is generally utilised in its conventionally administered amount.

Suitable methods of formulation include those described in the aforementioned European Patent Applications.

The following Examples illustrate the invention.

EXAMPLE 1 p-Nitrobenzyl (5R,6S)-3-(E-2-acetamidoethenylthio)-6-[(R)-1-azidoethyl]-7-oxo-1-azabicyclo[3.2.0]hept-2-ene-2-carboxylate

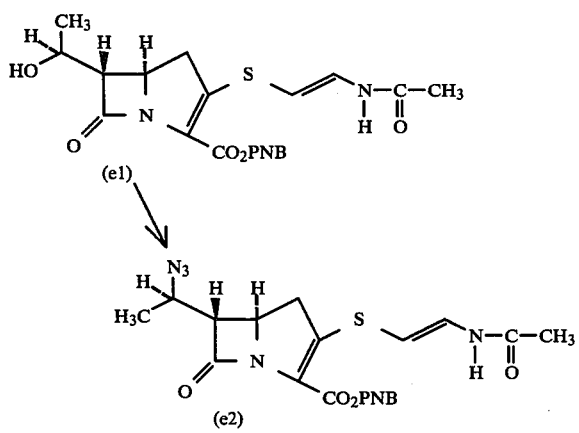

The ester (e1, 100 mg, 0.224 mM) was dissolved in dry tetrahydrofuran (30 ml) and cooled to 0° C. Triphenylphosphine (117 mg, 0.448 mM) was added with stirring, following by a solution of hydrazoic acid in toluene (0.68 ml, 0.68 M solution, 0.448 mM). Diethylazodicarboxylate (78 mg, 0.448 mM) in dry tetrahydrofuran (5 ml) was added and the reaction solution stirred at room temperature for 15 minutes. The solvent was removed at reduced pressure and the residue partitioned between ethyl acetate and water. The organic layer was washed with saturated sodium chloride solution and dried over anhydrous magnesium sulphate. Removal of the solvent at reduced pressure afforded a yellow oil, which was chromatographed over silica gel (type 60, 8 gm). Elution with ethyl acetate gave the product, contaminated with triphenylphosphine oxide, as a colourless oil (109 mg). Column chromatography over silica gel (10 gm), eluting with chloroform gave the pure p-nitrobenzyl (5R,6S)-3-(E-2-acetamidoethenylthio)-6-[(R)-1-azidoethyl]-7-oxo-1-azabicyclo[3.2.0]hept-2-ene-2-carboxylate (e2) as a colourless oil (21 mg). Trituration with ethyl acetate/diethyl ether gave a white solid, $\lambda_{max}$ (EtOH) 325 nm, 261 nm, $\nu_{max}$ (CHCl$_3$) 3430, 2110, 1780, 1700, 1621, 1608 cm$^{-1}$, $\delta_H$ (CDCl$_3$) 8.22 (2H, d, aromatic protons), 7.65 (2H, d, aromatic protons), 7.53 (1H, d, NH), 7.26 (1H, dd, HC=CHNH), 5.88 (1H, d, HC=CHNH), 5.38 (2H, q, CH$_2$Ar), 4.13 (1H, dt, 5-CH), 3.93 (1H, dq, 8-CH), 2.95–3.3 (2H, ABX, 4-CH$_2$), 3.16 (1H, dd, J 8.6 Hz and 2.9 Hz, 6-CH), 2.09 (3H, s, NHCOCH$_3$), 1.45 (3H, d, CH$_3$CH).

EXAMPLE 2

(5R,6R)-3-[E-2-acetamidoethenylthio]-6-[(R)-1-aminoethyl]-7-oxo-1-azabicyclo[3.2.0]hept-2-ene-2-carboxylic acid

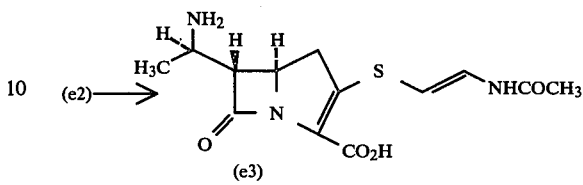

The azido derivative (e2) (15 mg) was dissolved in 1,4-dioxan (4 ml), water (0.6 ml), ethanol (0.15 ml) and 0.05 M pH 7.0 phosphate buffer (0.75 ml) and hydrogenated in the presence of 5% palladium on carbon (25 mg) catalyst for 2 hours. The suspension was filtered over Celite, washing well with water (25 ml). The filtrate was concentrated to about 20 ml and washed with ethyl acetate (3×50 ml). The aqueous solution was further concentrated to approximately 5 ml and chromatographed over Biogel P2, eluting with water. Fractions containing the title compound (e3) were identified by the chromophore at $\lambda_{max}$ (H$_2$O) 307 nm in the uv spectrum and were combined to yield an aqueous solution of the product (1.9 mg), $\lambda_{max}$ (H$_2$O) 307 nm, 230 nm.

EXAMPLE 3 p-Nitrobenzyl (5R,6S)-3-(E-2-acetamidoethenylthio)-6-[(R)-1-formyloxyethyl]-7-oxo-1-azabicyclo[3.2.0]hept-2-ene-2-carboxylate

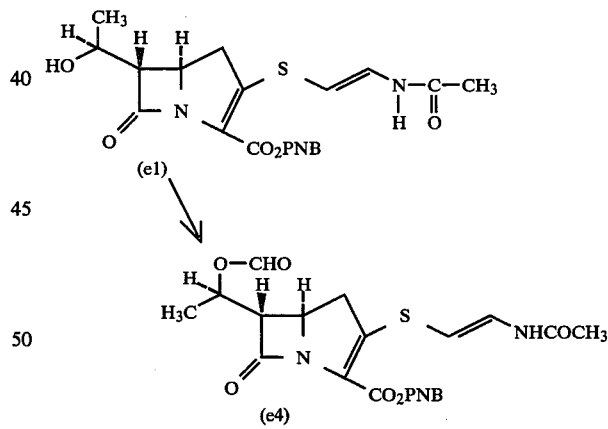

The ester (e1, 200 mg, 0.448 mM) was dissolved in dry tetrahydrofuran (50 ml) and cooled to 0° C. Triphenylphosphine (234 mg, 0.896 mM) was added with stirring, followed by a solution of formic acid (42 mg, 0.896 mM) in dry tetrahydrofuran (5 ml). Diethylazodicarboxylate (156 mg, 0.896 mM) in dry tetrahydrofuran (5 ml) was added and the reaction solution stirred at room temperature for 15 minutes. The solvent was evaporated at reduced pressure and the residue partitioned between ethyl acetate and water. The organic layer was washed with saturated sodium chloride solution and dried over anhydrous magnesium sulphate. Removal of the solvent at reduced pressure gave a pale yellow oil, which was chromatographed over silica gel (30 mg). Elution with ethyl acetate gave the impure product as a colourless oil (91 mg). This oil crystallized with ethyl acetate to yield a white solid (29 mg). Digesting in hot ethyl acetate, followed by filtration afforded the pure p-nitrobenzyl (5R,6S)-3-(E-2-acetamidoethenylthio)-6-[(R)-1-formyloxyethyl]-7-oxo-1-azabicyclo[3.2.0]hept-2-ene-2-carboxylate (e4) as a white solid (24 mg), $\lambda_{max}$ (EtOH) 324 nm, 261 nm, $\nu_{max}$ (CHBr$_3$) 3260, 1782, 1703, 1672, 1625 cm$^{-1}$, $\delta_H$ (d$_7$-DMF) 10.48 (1H, d, NH), 8.31 (1H, s, CHO), 8.28 (2H, d, aromatic protons), 7.82 (2H, d, aromatic protons), 7.20 (1H, dd, d with D$_2$O, HC=CH—NH), 5.99 (1H, d, S—CH=CH), 5.46 (2H, q, CH$_2$Ar), 5.34 (2H, m, 8-CH), 4.29 (1H, dt, 5-CH), 3.81 (1H, dd, J 2.7 Hz and 5.9 Hz, 6-CH), 3.31 (2H, d, 4-CH$_2$) 2.02 (3H, s, NHCOCH$_3$), 1.36 (3H, d, CH$_3$CH). CL EXAMPLE 4

EXAMPLE 4 p-Nitrobenzyl (5R,6S)-3-(E-2-acetamidoethenylthio)-6-[(R)-1-hydroxyethyl]-7-oxo-1-azabicyclo[3.2.0]hept-2-ene-2-carboxylate

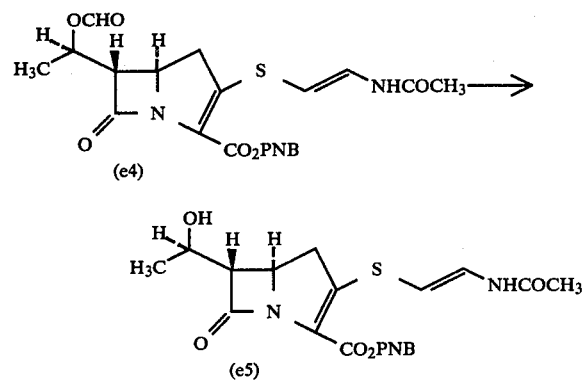

The formate ester (e4, 425 mg, 0.89 mM) was dissolved in 20% aqueous 1,4-dioxan (80 ml) and cooled to 0° C. 0.1 N Sodium hydroxide solution (10.74 ml, 1.07 mM) was added and stirring continued for 5 minutes. Ethylacetate (150 ml) was then added and the organic solution washed with water, saturated sodium chloride solution and dried over anhydrous magnesium sulphate. After filtration, the solvent was removed to yield a pale yellow solid. This solid was chromatographed over silica gel (15 gm). Elution with 10% ethanol/chloroform gave the pure p-nitrobenzyl (5R,6S)-3-(E-2-acetamidoethenylthio)-6-[(R)-1-hydroxyethyl]-7-oxo-1-azabicyclo [3.2.0]hept-2-ene-2-carboxylate (e5) as a white solid. This solid was digested in dry diethyl ether and collected by filtration (100 mg), $\lambda_{max}$(EtOH) 325 nm ($\epsilon$m 16880), 263 nm ($\epsilon$m 17968), $\nu_{max}$(KBr) 3420, 3260, 1778, 1700, 1675, 1624, 1554, 1520, 1380, 1350, 1335 cm$^{-1}$; $\delta_H$(d$_7$-DMF) 10.50 (1H, d. J 10 Hz, NH), 8.30 (2H, d, aromatic protons), 7.85 (2H, d, aromatic protons), 7.22 (1H, dd, J 10 Hz and 14 Hz, NHCH=CH), 6.02 (1H, d, J 14 Hz), 5.47 (2H, q, CH$_2$Ar), 4.28 (dt, 1H, J 3 Hz and 9 Hz, 5-CH), 4.08 (1H, dq, 8-CH), 3.43 (1H, dd, J 3 Hz and 6.3 Hz, 6-CH), 3.27 (2H, ABX, 4-CH$_2$) 2.03 (3H, s, COCH$_3$), 1.23 (3H, d, J 6 Hz, CH$_3$CH).

EXAMPLE 5

Sodium (5R,6S)-3-(E-2-acetamidoethenylthio)-6-[(R)-1-hydroxyethyl]-7-oxo-1-azabicyclo[3.2.0]hept-2-ene-2-carboxylate

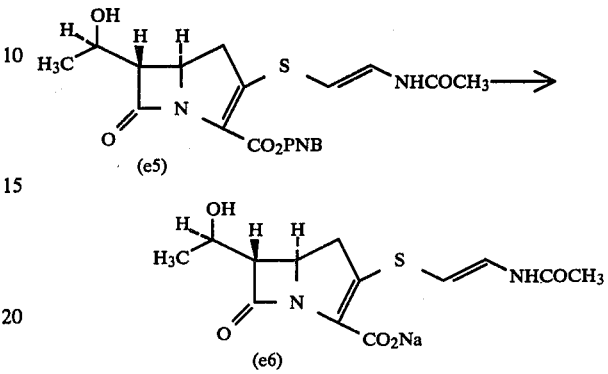

5% Palladium on charcoal catalyst (16 mg) was shaken with hydrogen in 30% aqueous 1,4-dioxan (10 ml) at ambient temperature and pressure for 20 minutes. A solution of the ester (e5, 12 mg, 0.027 mM) in 1,4-dioxan (2 ml) was added and the hydrogenation was continued for a further 3 h. Sodium bicarbonate (2.3 mg) was added and the solution filtered through Celite, washing well with water (25 ml). The filtrate was concentrated at reduced pressure to approximately 15 ml and washed with ethylacetate (3×20 ml). The aqueous solution was then freeze-dried to yield the title compound (e6) as a pale yellow fluffy solid, $\lambda_{max}$(H$_2$O) 307 nm, 227 nm, $\nu_{max}$(KBr) 3400, 1750, 1670, 1620 cm$^{-1}$.

EXAMPLE 6

Sodium (5R,6S)-3-(E-2-acetamidoethenylthio)-6-[(R)-1-formyloxyethyl]-7-oxo-1-azabicyclo[3.2.0]hept-2-ene-2-carboxylate

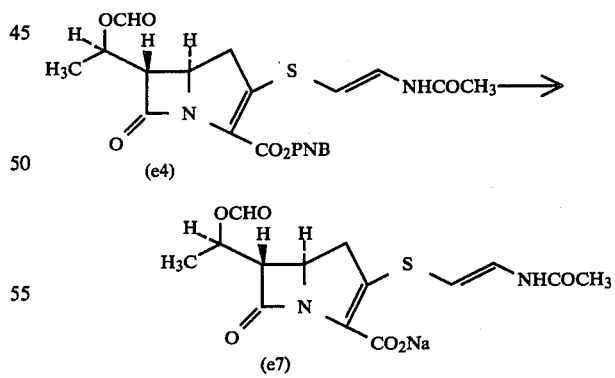

The formate ester (e4, 10 mg) was dissolved in 30% aqueous 1,4-dioxan (10 ml) and shaken with hydrogen in the presence of 5% palladium on carbon catalyst (15 mg) for 3.5 hours. Sodium bicarbonate (2.3 mg) was then added and the solution filtered through Celite, washing well with water (20 ml). The filtrate was concentrated at reduced pressure to approximately 15 ml and washed with ethylacetate (3×20 ml). The resulting aqueous solution was estimated to contain 2.2 mg of the title compound (e7) based on εm 14,000 at λ$_{max}$ 307 nm in the uv spectrum,λ$_{max}$(H$_2$O) 307 nm 229 nm.

EXAMPLE 7 p-Nitrobenzyl (5R,6S)-3-(2-acetamidoethylthio)-6-[(R)-1-azidoethyl]-7-oxo-1-azabicyclo[3.2.0]hept-2-ene-2-carboxylate

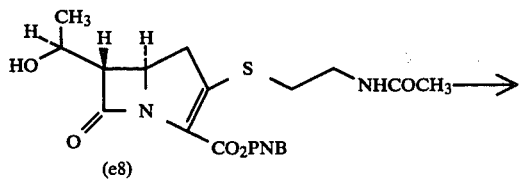
(e8)

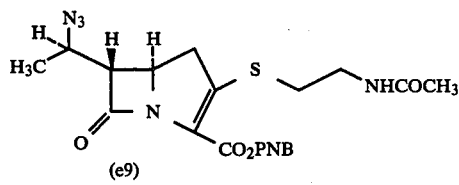
(e9)

The compound (e8) (300 mg; 0.067 mM) was suspended in dry tetrahydrofuran (100 ml) and cooled to 0° C. Triphenylphosphine (351 mg) was added with stirring, followed by a solution of hydrazoic acid in toluene (0.68 M solution; 2.1 ml). Diethylazodicarboxylate (234 mg) in dry tetrahydrofuran (5 ml) was added and the reaction stirred at room temperature for 30 minutes. The solvent was removed at reduced pressure and the residue partitioned between ethyl acetate and water. The organic layer was washed with saturated sodium chloride solution and dried over anhydrous magnesium sulphate. Removal of the solvent at reduced pressure afforded a pale yellow solid which was chromatographed over silica gel (10 gm). Elution with ethylacetate gave the title compound (e9) as a white solid. This solid was digested in ethylacetate and collected by filtration (80 mg), mp 167°–170° C., λ$_{max}$ (EtOH) 319 nm (εm, 13,591), 266 nm (εm 11,656), ν$_{max}$ (KBr) 3275, 2120, 1785, 1700, 1630, 1607, 1545, 1517, 1340 (broad) cm$^{-1}$, δ$_H$ (d$_7$-DMF) 8.26 (2H, d, aromatic protons), 8.10 (broad res., exchanges with D$_2$O, NH), 7.81 (2H, d, aromatic protons), 5.45 (2H, q, CH$_2$Ar), 4.0–4.4 (2H, m, 5-CH+8-CH), 3.65 (1H, dd, J 3 Hz and 7 Hz, 6-CH), 3.2–3.6 (m, SCH$_2$CH$_2$), 3.08 (2H, d, 4-CH$_2$), 1.88 (3H, s, COCH$_3$), 1.39 (3H, d, CH$_3$CH).

EXAMPLE 8

(5R,6R)-3-(2-Acetamidoethylthio)-6-[(R)-1-aminoethyl]-7-oxo-1-azabicyclo[3.2.0]hept-2-ene-2-carboxylic acid

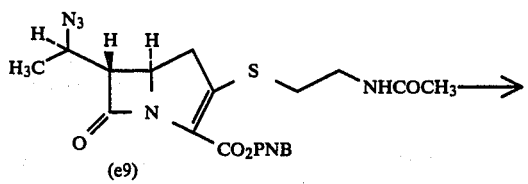
(e9)

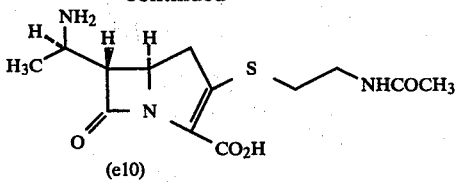
(e10)

The azido derivative (e9, 50 mg) was dissolved in 1,4-dioxan (12 ml), water (2 ml), ethanol (0.45 ml) and pH 7.0 phosphate buffer (2.25 ml) and hydrogenated in the presence of 5% palladium on carbon (75 mg) for 2 hours at ambient temperature and pressure. The suspension was filtered through Celite, washing well with water. The filtrate was concentrated to about 25 ml and washed with ethylacetate (3×50 ml). The aqueous solution was further concentrated to approximately 5 ml and chromatographed over Biogel P2, eluting with water. Fractions containing the title compound (e10) were identified by the chromophore at λ$_{max}$(H$_2$O) 298 nm in the UV spectrum and were combined to yield an aqueous solution of the product (7.8 mg). A sample of the solution was freeze-dried to yield a pale yellow solid, λ$_{max}$ (H$_2$O) 298 nm, ν$_{max}$(KBr) 3200 (broad), 1750 cm$^{-1}$.

EXAMPLE 9 p-Nitrobenzyl (5R,6S)-6-[(R)-1-formyloxyethyl]-3-(2-pyrimidylthio)-7-oxo-1-azabicyclo[3.2.0]hept-2-ene-2-carboxylate

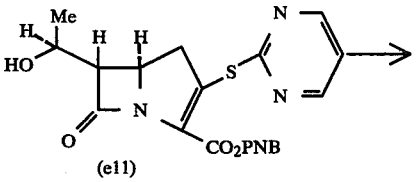
(e11)

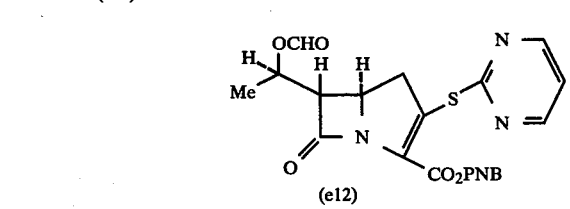
(e12)

The 5R,6S,8S-derivative (e11) (95 mg) was dissolved in dry THF (5 ml) and the solution was cooled to 0° C. To the solution was successively added triphenylphosphine (112 mg), formic acid (55 mg) and diethylazodicarboxylate (75 mg) with stirring at 0° C. The solution was allowed to warm to room temperature and after a further 15 mins ethylacetate (30 ml) was added. The solution was washed with dilute NaHCO$_3$ solution (20 ml), water (20 ml) and brine (20 ml) and then dried (MgSO$_4$). Evaporation of the solvent gave a crude product which was chromatographed on silica gel using a gradient elution of 50%→20% petrolethylacetate. The first-eluted product (49 mg) contained ca 50% of p-nitrobenzyl (5R,6S)-6-[(R)-1-formyloxyethyl]-3-(2-pyrimidylthio)-7-oxo-1-azabicyclo[3.2.0]hept-2-ene -2-carboxylate (e12); λ$_{max}$ (EtOH) 320 and 263 nm; ν$_{max}$ (CH$_2$Cl$_2$) 1780, 1725 and 1700 sh cm$^{-1}$; δ(CDCl$_3$) 1.45 (3H, d, J 6.5 Hz, MeCH), 3.22 (1H, dd, J 18 and 9 Hz, 4-CHa), 3.45 (1H, dd, J 3 and 7.5 Hz, 6-CH), 3.86 (1H, dd, J 18 and 10 Hz, 4-CHb), 4.31 (1H, approx. dt, J 3 and 9.5 Hz, 5-CH), 5.27 and 5.52 (each 1H, d, J 14 Hz, CH$_2$Ar), ca 5.40 (1H, m, CHMe), 7.12 (1H, t, J 5 Hz, pyrimidine-CH), 7.65 and 8.21 (each 2H, d, J 9Hz, ArCH$_2$), 8.07 (1H, s, OCHO), and 8.58 (2H, d, J 5 Hz, 2×pyrimidine-CH) [M+, 470.0876. C$_{21}$H$_{18}$N$_4$O$_7$S requires M, 470.0895].

EXAMPLE 10 p-Nitrobenzyl (5R,6S)-6-[(R)-1-hydroxyethyl]-3-(2-pyrimidinylthio)-7-oxo-1-azabicyclo[3.2.0]hept-2-ene-2-carboxylate

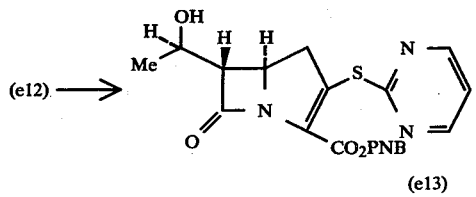

(e13)

A solution of the derivative (e12) (45 mg) in 20% aqueous dioxan (5 ml) was treated with a solution of 0.1 N NaOH (1.5 ml) at 5° C. for 3 mins. Ethylacetate (30 ml) was added and the organic solution was washed with pH 7 buffer (20 ml), water (20 ml) and brine (20 ml). Evaporation of the dried (MgSO$_4$) organic layer gave a crude product which was chromatographed on silica gel using a gradient elution of 20% petrol-ethylacetate to ethylacetate. p-Nitrobenzyl (5R,6S)-6-[(R)-1-hydroxyethyl]-3-(2-pyrimidinylthio)-7-oxo-1-azabicyclo[3.2.0]hept-2-ene-2-carboxylate (e13) was obtained as a white solid (7 mg); m.p. 153°–55° (from EtOAc-Et$_2$O); λ$_{max}$ (EtOH) 320 (14,295) and 262 nm (14,295); ν$_{max}$ (KBr) 1775 and 1700 cm$^{-1}$; δ (CDCl$_3$) 1.38 (3H, d, J 6.5 Hz, MeCH), 1.87 (1H, brs, OH), 3.25 (1H, dd, J 9 and 18 Hz, 4-CHa), 3.30 (1H, dd, J 3 and 7 Hz, 6-CH), 3.86 (1H, dd, J 10 and 18 Hz, 4-CHb), ca 4.30 (1H, m, CHMe), 4.37 (1H, dt, J 3 and 9.5 Hz, 5-CH), 5.31 and 5.52 (each 1H, d, J 14 Hz, CH$_2$Ar) 7.13 (1H, t, J 5 Hz, pyrimidine-CH), 7.67 and 8.24 (each[2] 2H, d, J 9 Hz, CH$_2$Ar), and 8.61 (2H, d, J 5 Hz, 2×pyrimidine-CH).

EXAMPLE 11

Sodium (5R,6S)-6-[(R)-1-hydroxyethyl]-3-(2-pyrimidinylthio)-7-oxo-1-azabicyclo[3.2.0]hept-2-ene-2-carboxylate

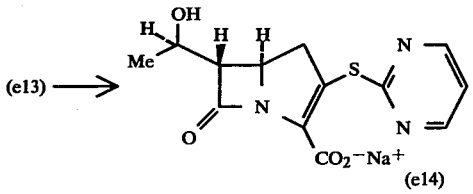

(e14)

5% Palladium on carbon catalyst (15 mg) was prehydrogenated in 30% aqueous dioxan (10 ml) at ambient temperature for 30 mins. To the mixture was added a solution of the ester (e13) (10 mg) in dioxan (1 ml) and hydrogenation was continued for 2 h. Sodium bicarbonate (2.5 mg) was added and the mixture was filtered over Celite washing the pad well with water (20 ml). The solution was concentrated to ca 20 ml and then washed with ethyl acetate (3×20 ml). The aqueous layer was freeze-dried to afford the title compound (e14) (5 mg); λ$_{max}$ (H$_2$O) 296 and 246 nm; ν$_{max}$ (KBr) 1755 and 1600 cm$^{-1}$.

EXAMPLE 12

Sodium (5R,6S)-6-[(R)-1-formyloxyethyl]-3-(2-pyrimidinylthio)-7-oxo-1-azabicyclo[3.2.0]hept-2-ene-2-carboxylate

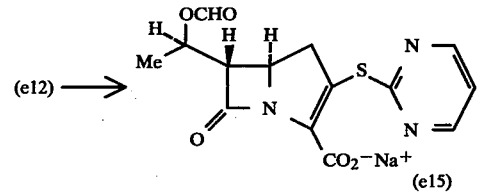

(e15)

The derivative (e12) (15 mg) was hydrogenolysed in the manner described in Example 11 to afford the title salt (e15) (6 mg); λ$_{max}$ (H$_2$O) 295 and 245 nm; ν$_{max}$ (KBr) 1760, 1720 and 1600 cm$^{-1}$.

EXAMPLE 13

Preparation of Sodium (5R,6S)-3-(E-acetamidoethenylthio)-6-[(R)-1-hydroxyethyl]-7-oxo-1-azabicyclo[3.2.0]hept-2-ene-2-carboxylate (e6) directly from p-nitrobenzyl (5R,6S)-3-(E-2-acetamidoethenylthio)-6-[(R)-1-formyloxyethyl]-7-oxo-1-azabicyclo[3.2.0]hept-2-ene-2-carboxylate (e4)

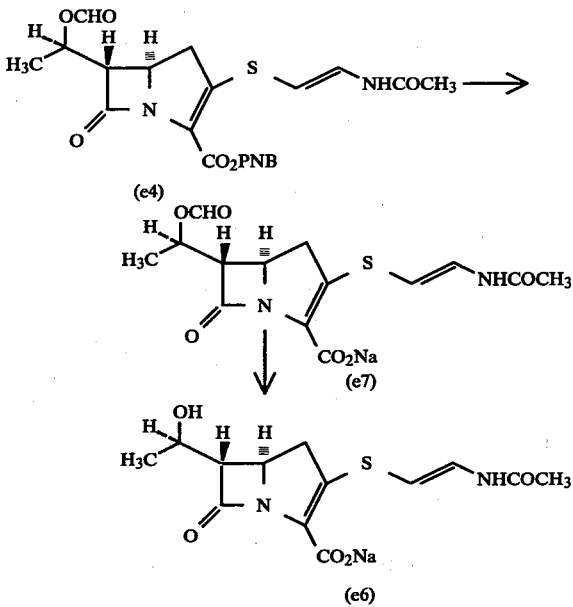

5% Palladium on carbon catalyst (600 mg) was suspended in 30% aqueous 1,4-dioxan (75 ml) and shaken with hydrogen at ambient temperature and pressure for 0.5 h. A suspension of the ester (e4, 400 mg, 0.842 mM) in 30% aqueous 1.4-dioxan (25 ml) was then added to the vessel. The resulting suspension was shaken with hydrogen at ambient temperature and pressure for 3.5 h. Sodium bicarbonate (71 mg, 0.842 mM) was added and the solution filtered through Celite, washing well with water (100 ml). The filtrate was concentrated at reduced pressure to approximately 100 ml and washed with ethyl acetate (3×150 ml). The resulting aqueous solution of sodium (5R,6S)-3-(E-2-acetamidoethenylthio)-6-[(R)-1-formyloxyethyl]-7-oxo-1-azabicyclo[3.2.0-]hept-2-ene-2-carboxylate (e7) was adjusted to pH 8.0 with saturated sodium bicarbonate solution and stirred at room temperature for 16 h. The solution was then concentrated at reduced pressure and chromatographed over Diaion HP20, eluting with water. The column fractions were monitored by U.V. and H.P.L.C. (10% CH$_3$CN, 90% 0.05 M, pH 4.7 ammonium dihydrogen orthophosphate buffer; 2 ml.min$^{-1}$; $\lambda_{max}$ 300 nm; 300 mm.h$^{-1}$; Abs 0.16). Fractions 10 to 22 contained pure sodium (5R,6S)-3-(E-2-acetamidoethenylthio)-6-[(R)-1-hydroxyethyl]-7-oxo-1-azabicyclo[3.2.0]hept-2-ene-2-carboxylate (e6). These fractions were combined and freeze dried to yield a white fluffy solid. (89 mg), $[\alpha]_D^{20}+78.3°$ (C, 0.592 H$_2$O), $\nu_{max}$ (KBr) 3400 (broad) 1750, 1670, 1590~1620 cm$^{-1}$, $\lambda_{max}$ (H$_2$O) 307 nm ($\epsilon$m 13,296), 228 nm ($\epsilon$m 12,570), $\delta_H$ (D$_2$O) 1.08 (3H, d, J 6 Hz, C$\underline{H}_3$CH), 1.86 (3H, s, COC$\underline{H}_3$), 2.925 (2H, ABX, J$_{4a5}$ 8.5 Hz, J$_{4b5}$ 9.7 Hz, J$_{4a4b}$ 18 Hz, 4-C$\underline{H}_2$), 3.165 (1H, dd, J$_{56}$ 2.5 Hz, J$_{68}$ 6.0 Hz, 6-C$\underline{H}$), 3.96 (1H, dt, J$_{56}$ 2.5 Hz, 5-C$\underline{H}$), 4.00 (1H, apparent quintet, 8-C$\underline{H}$), 5.815 (1H, d, J 13 Hz, C=C$\underline{H}$—S), 6.945 (1H, d, J 13 Hz, N—C$\underline{H}$=C).

Fractions 23 to 51 were found to contain mixtures of sodium (5R,6S)-3-(E-2-acetamidoethenylthio)-6-[(R)-1-hydroxyethyl]-7-oxo-1-azabicyclo[3.2.0]hept-2-ene-2-carboxylate (e6) and sodium (5R,6S)-3-(E-2-acetamidoethenylthio)-6-[(R)-1-formyloxyethyl]-7-oxo-1-azabicyclo[3.2.0]hept-2-ene-2-carboxylate (e7). They were, therefore, combined and stirred for a further 16 h at room temperature and pH 8.5 (sodium bicarbonate solution). HPLC then indicated that the hydrolysis had proceeded to completion. The solution was therefore concentrated at reduced pressure and chromatographed over Diaion HP20, eluting with water. Fraction 14 to 31 were combined and freeze dried to yield an additional quantity of the title compound (e6) as a pale yellow solid (29 mg).

EXAMPLE 14

Preparation of Sodium (5R,6S)-3-(Z-2-acetamidoethenylthio)-6-[(R)-1-hydroxyethyl]-7-oxo-1-azabicyclo[3.2.0.]hept-2-ene-2-carboxylate (e18) directly from p-nitrobenzyl (5R,6S)-3-(Z-2-acetamidoethenylthio)-6-[(R)-1-formyloxyethyl]-7-oxo-1-azabicyclo[3.2.0]hept-2-ene-2-carboxylate (e16)

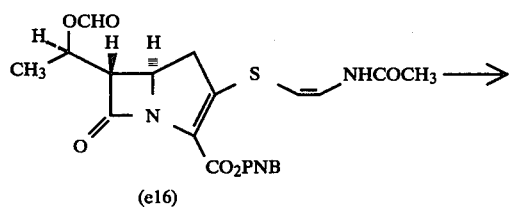
(e16)

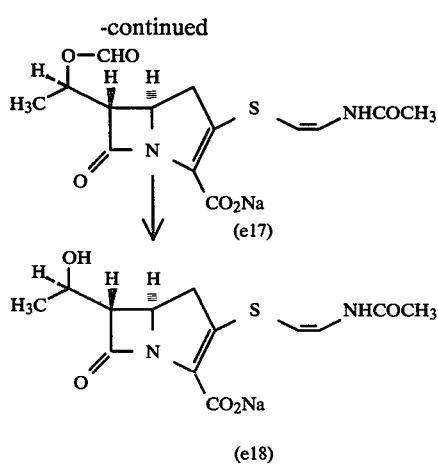
(e17)

(e18)

Sodium (5R,6S)-3-(Z-2-acetamidoethenylthio)-6-[(R)-1-hydroxyethyl]-7-oxo-1-azabicyclo[3.2.0.]hept-2-ene-2-carboxylate (e18) was prepared as a pale yellow solid, after freeze drying from the ester (e16) by the procedure described in Example 13, $\lambda_{max}$ (H$_2$O) 306 nm ($\epsilon$m 11,611) 230 nm ($\epsilon$m 11,647), $\nu_{max}$ (KBr) 3400 (broad), 1755, 1678, 1590~1630 cm$^{-1}$, $\delta_H$(D$_2$O) 1.07 (3H, d, J 6.4 Hz, C$\underline{H}_3$CH), 1.92 (3H, s, COC$\underline{H}_3$), 2.93 (2H, ABX, J$_{4a4b}$ 18 Hz, J$_{4a5}$ 9.75 Hz, J$_{4b5}$ 8.5 Hz, 4-C$\underline{H}_2$), 3.17 (1H, dd, J$_{56}$ 2.5 Hz, J$_{68}$ 5.8 Hz, 6-C$\underline{H}$), 3.97 (1H, dt, 5-C$\underline{H}$) overlapping with 4.01 (1H, apparent quintet, 8-C$\underline{H}$), 5.47 (1H, d, J 7.5 Hz, C=C$\underline{H}$—S), 6.93 (1H, d, J 7.5 Hz, N—C$\underline{H}$=C).

EXAMPLE 15 p-Nitrobenzyl (5R,6S)-3-(2-acetamidoethylthio)-6-[(R)-1-formyloxyethyl]-7-oxo-1-azabicyclo[3.2.0]hept-2-ene-2-carboxylate

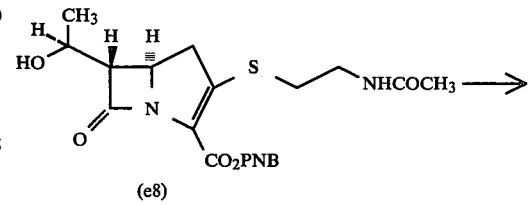
(e8)

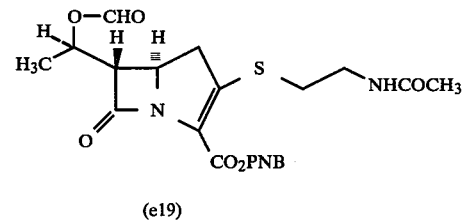
(e19)

The title compound (e19) was prepared as a white crystalline solid from compound (e8), by the procedure described in Example 3, mp 175°–178° C. (EtoAc), (Found: C, 52.79; H, 4.89; N, 8.75. C$_{21}$H$_{23}$N$_3$O$_8$S requires: C, 52.82; H, 4.86; N, 8.80%), $\lambda_{max}$ (CH$_3$CN) 318 nm ($\epsilon$m 12,970) 268 nm ($\epsilon$m 11,175), $\nu_{max}$ (CHBr$_3$) 3270, 1788, 1702, 1625 cm$^{-1}$, $\delta_H$(d$_7$-DMF) 1.40 (3H, d, C$\underline{H}_3$CH), 1.90 (3H, s, COC$\underline{H}_3$), 3.08 (2H, m, SCH$_2$), 3.38–3.64 (4H, ABX+q, 4-C$\underline{H}_2$+N—C$\underline{H}_2$), 3.84 (1H, dd, J$_{56}$ 2.9 Hz, J$_{68}$ 5.9 Hz, 6-CH), 4.34 (1H, dt, 5-C$\underline{H}$), 5.37 (1H, m, 8-C$\underline{H}$), 5.47 (2H, q, C$\underline{H}_2$Ar), 7.83 (2H, d, aromatic protons), 8.21 (1H, broad t, NH), 8.29 (2H, d, aromatic protons, 8.34 (1H, s, C<u>H</u>O).

EXAMPLE 16 p-Nitrobenzyl (5R,6S)-3-(2-acetamidoethylthio)-6-[(R)-1-hydroxyethyl]-7-oxo-1-azabicyclo[3.2.0]hept-2-ene-2-carboxylate

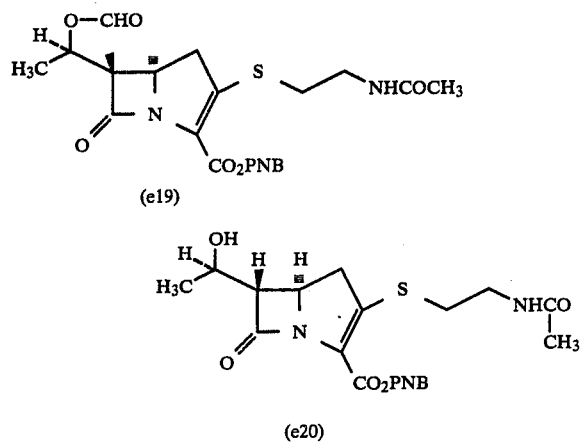

Hydrolysis of p-nitrobenzyl (5R,6S)-3-(2-acetamidoethylthio)-6-[(R)-1-formyloxyethyl]-7-oxo-1-azabicyclo[3.2.0]hept-2-ene-2-carboxylate (e19), following the procedure described in Example 4 afforded the title compound (e20) as a white crystalline solid, $\lambda_{max}$ (EtOH) 319 nm ($\epsilon_m$ 13,265) 265 nm (m 11,580), $\nu_{max}$ (KBr) 3400, 3290, 1778, 1700, 1641, 1608, 1548, 1518, 1349, 1335 cm$^{-1}$, $\delta_H$(d$_7$-DMF) 1.24 (3H, d, CH$_3$C<u>H</u>), 1.88 (3H, s, COC<u>H</u>$_3$), 3.02 (2H, m, SC<u>H</u>$_2$), 3.3–3.6 (5H, ABX+dd+q, 4-C<u>H</u>$_2$+6-CH+NC<u>H</u>$_2$, $J_{4a4b}$ 18.25 Hz, $J_{4a5}$ 9.75 Hz, $J_{4b5}$ 8.5 Hz, $J_{68}$ 6.1 Hz, $J_{56}$ 2.9 Hz), 4.08 (1H, apparent quintet, 8-C<u>H</u>), 4.29 (1H, dt, $J_{56}$ 2.9 Hz, 5-C<u>H</u>), 5.45 (2H, q, C<u>H</u>$_2$Ar), 7.83 (2H, d, aromatic protons), 8.19 (1H, broad t, N<u>H</u>), 8.28 (2H, d, aromatic protons).

EXAMPLE 17

Sodium (5R,6S)-3-(2-acetamidoethylthio)-6-[(R)-1-hydroxyethyl]-7-oxo-1-azabicyclo[3.2.0]hept-2-ene-2-carboxylate

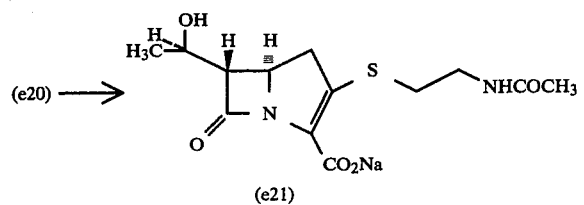

The ester (e20) was hydrogenolysed as in Example 5 to yield the title compound (e21) as a white fluffy solid after HP20 column chromatography and lyophilisation, $[\alpha]_D^{20}$+60° (c, 0.45 H$_2$O), $\nu_{max}$ (KBr) 3400 (broad), 1750, 1610–1660 (broad), 1588, 1555 (shoulder), 1400 cm$^{-1}$, $\lambda_{max}$(H$_2$O) 299 nm ($\epsilon_m$ 6366), $\delta_H$(D$_2$O) 1.08 (3H, d, J 6.5 Hz, CH$_3$CH), 1.78 (3H, s, COC<u>H</u>$_3$), 2.73 (2H, tq, SC<u>H</u>$_2$), 2.97 (2H, ABX, $J_{4a4b}$ 17.5 Hz, $J_{4a5}$ 9.5 Hz, $J_{4b5}$ 8.75 Hz, 4-C<u>H</u>$_2$), 3.13–3.23 (3H, dd+t, $J_{56}$2.5 Hz, $J_{68}$ 6.0 Hz, 6-C<u>H</u>+N—C<u>H</u>$_2$), 3.92–4.07 (2H, dt+apparent quintet, 5-C<u>H</u>+8-C<u>H</u>).

EXAMPLE 18 p-Nitrobenzyl (5R,6S)-3-(Z-2-p-nitrobenzyloxycarbonylethenylthio)-6-[(R)-1-formyloxyethyl]-7-oxo-1-azabicyclo[3.2.0-]hept-2-ene-2-carboxylate

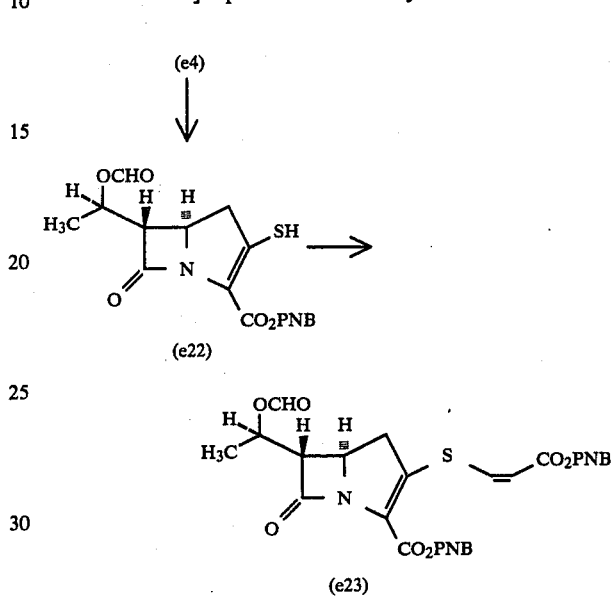

The ester (e4) (300 mg) was dissolved in 10% aqueous 1,4-dioxan (40 ml) and stirred at room temperature for 4.5 minutes with N-bromoacetamide (87 mg). The solution was then diluted with chloroform (200 ml) and washed with pH 7.0 phosphate buffer, saturated sodium chloride solution and dried over anhydrous magnesium sulphate. Filtration and removal of the solvent at reduced pressure afforded the intermediate thiol (e22) as a pale yellow gum, $\nu_{max}$ (CHCl$_3$) 1780, 1720, 1605 cm$^{-1}$.

The thiol (e22) was then dissolved in dry dimethylformamide (5 ml) and stirred at room temperature for 20 minutes with p-nitrobenzylpropiolate (389 mg) and anhydrous potassium carbonate (44 mg). The solution was diluted wth ethyl acetate and washed with water and saturated sodium chloride solution. The organic solution was dried over anhydrous magnesium sulphate, filtered and evaporated at reduced pressure to yield the crude product as an orange gum. This gum was chromatographed over silica gel (20 gm). Elution with 1:1 hexane/ethyl acetate furnished the title compound (e23) as a pale yellow solid (135 mg), $\nu_{max}$ (CHCl$_3$) 1781, 1718, 1605 cm$^{-1}$, $\lambda_{max}$(CH$_3$CN) 334 nm ($\epsilon_m$ 22759), 266 nm ($\epsilon_m$ 22346), $\delta_H$ (CDCl$_3$) 1.45 (3H, d, C<u>H</u>$_3$CH), 3.1–3.6 (3H, m, 4-C<u>H</u>$_2$+6-C<u>H</u>), 4.28 (1H, dt, 5-C<u>H</u>), 5.2–5.6 (5H, m, 2+C<u>H</u>$_2$Ar+8-CH), 6.05 (1H, d, J 10 Hz, C<u>H</u>=C), 7.30 (1H, d, C=C<u>H</u>), 7.5–7.75 (4H, aromatic protons), 8.03 (1H, s, C<u>H</u>O), 8.21 (4H, d, aromatic protons).

EXAMPLE 19

Disodium (5R,6S)-3-(Z-2-carboxyethenylthio)-6-[(R)-1-hydroxyethyl]-7-oxo-1-azabicyclo[3.2.0]hept-2-ene-2-carboxylate

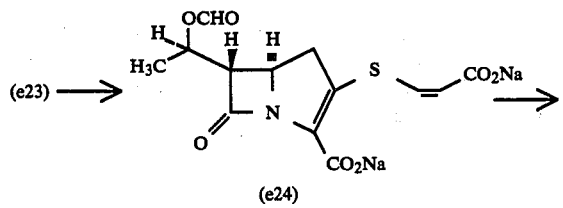

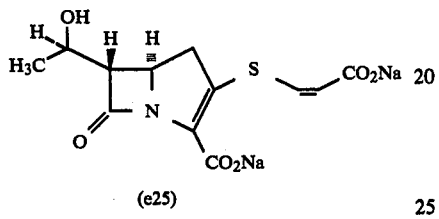

The ester (e23) (20 mg) was hydrogenolysed and the resulting formate ester-disodium salt (e24) hydrolysed, as in Example 13 to yield an aqueous solution containing the title compound (e25), (3 mg, assuming $\epsilon_m$ 17,000 at $\lambda_{max}$ 315 nm) after HP20 column chromatography, $\lambda_{max}$ (H$_2$O) 315 nm.

DEMONSTRATION

Antibacterial effectiveness of the compounds of the Examples in a standard microtitre test.

| Organism | MIC (μg/ml) Compound of Example | | | |
|---|---|---|---|---|
| | 2 | 5 | 6 | 8 |
| *Citrobacter freundii* E8 | 2.0 | 0.5 | 1.6 | 16 |
| *Enterobacter cloacae* N1 | 2.0 | 1.0 | 6.2 | 16 |
| *Escherichia coli* 0111 | 0.5 | ≦0.5 | 1.6 | 16 |
| *Escherichia coli* JT 39 | 0.5 | 0.2 | 0.8 | 8.0 |
| *Klebsiella aerogenes* A | 0.5 | 0.5 | 1.6 | 8.0 |
| *Proteus mirabilis* C977 | 4.0 | 2.0 | 6.2 | 31 |
| *Proteus morganii* I580 | 8.0 | 2.0 | 6.2 | 16 |
| *Proteus rettgeri* WM16 | 4.0 | 2.0 | 3.1 | 16 |
| *Proteus vulgaris* W091 | 4.0 | 2.0 | 3.1 | 16 |
| *Pseudomonas aeruginosa* A | 62 | 125 | 100 | 62 |
| *Salmonella typhimurium* CR10 | 1.0 | 0.5 | 3.1 | 8.0 |
| *Serratia marcescens* US20 | 2.0 | 2.0 | 3.1 | 16 |
| *Shigella sonnei* MB 11967 | 1.0 | ≦1.0 | 1.6 | 8.0 |
| *Bacillus subtilis* A | 0.2 | 0.2 | 0.8 | 4.0 |
| *Staphylococcus aureus* Oxford | 0.5 | 0.2 | 0.8 | 4.0 |
| *Staphylococcus aureus* Russell | 0.5 | ≦0.5 | 0.4 | 2.0 |
| *Staphylococcus aureus* 1517 | 8.0 | — | 12.5 | 31 |
| *Streptococcus faecalis* I | 4.0 | 8.0 | 12.5 | 16 |
| *Streptococcus pneumoniae* CN33 | — | 0.2 | 0.1 | 2.0 |
| *Streptococcus pyogenes* CN10 | — | 0.5 | 0.2 | 2.0 |
| *Escherichia coli* ESS | 0.2 | >0.2 | 0.4 | 4.0 |
| *Escherichia coli* JT 4 R+ | 2.0 | — | — | — |
| *Klebsiella aerogenes* Ba 95 R+ | 2.0 | — | — | — |

We claim:
1. A process for the preparation of a compound of the formula (II):

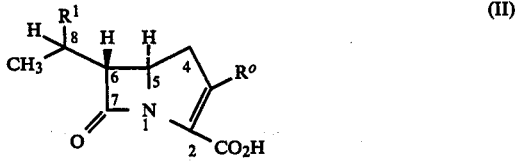

or a pharmaceutically acceptable salt or in vivo hydrolyzable ester thereof, wherein $R^1$ is azido, amino or hydroxy, or is a group of the sub-formula (a):

$$-OCOR^3 \quad (a)$$

wherein $R^3$ is hydrogen or $C_{1-6}$ alkyl, aryl or aryl ($C_{1-6}$) alkyl; and $R^o$ is hydrogen or $-S(O)_xR^2$, wherein x is zero or one and $R^2$ is $C_{1-6}$ alkyl, unsubstituted or monosubstituted by amino, di-($C_{1-6}$ alkyl) amino, $C_{1-6}$ alkyl amino, acylamino, hydroxy, $C_{1-6}$ alkanoyloxy, $C_{1-6}$ alkoxy, benzoyl, $C_{1-6}$-alkanoyl or carboxy or an ester or pharmaceutically acceptable salt thereof; $C_{2-6}$ alkenyl, unsubstituted or monosubstituted by hydroxy, $C_{1-6}$ alkoxy, acetamido, propionamido or carboxy or an ester or pharmaceutically acceptable salt thereof; $C_{2-6}$ alkynyl; $C_{1-6}$ alkanoyl; phenyl, naphthyl, pyrrolyl, furyl, tetrazolyl, thienyl, indolyl, thionaphthyl, benzofuryl, imidazolyl or thiazolyl, each of which being unsubstituted or monosubstituted by $C_{1-3}$ alkyl, phenyl, nitro, amino or phenyl substituted by halogen, $C_{1-3}$ alkoxy or acetamido; phenyl $C_{1-6}$ alkyl, unsubstituted or monosubstituted by halogen, $C_{1-3}$ alkoxy, nitro or acetamido; pyrrolyl $C_{1-6}$-alkyl, unsubstituted or monosubstituted by phenyl or $C_{1-3}$-alkyl; thienyl $C_{1-6}$ alkyl, unsubstituted or monosubstituted by phenyl or $C_{1-3}$ alkyl; furyl $C_{1-6}$ alkyl, unsubstituted or monosubstituted by phenyl or $C_{1-3}$ alkyl; tetrazolyl $C_{1-6}$-alkyl, unsubstituted or monosubstituted by phenyl or $C_{1-3}$-alkyl; imidazolyl $C_{1-6}$ alkyl, unsubstituted or monosubstituted by phenyl, nitro, amino or $C_{1-3}$ alkyl; thiazolyl $C_{1-6}$ alkyl, unsubstituted or monosubstituted by one or more phenyl, nitro, amino or $C_{1-3}$ alkyl; phenyl $C_{1-6}$ alkanoyl; phenoxy $C_{1-6}$ alkanoyl; or benzoyl; which comprises the reaction of an ester of a compound of the formula (III):

wherein the stereochemistry at C-8 is inverted compared to that at C-8 of the compound of the formula (II), with (a) a compound of the formula (IV):

$$R^4-H \quad (IV)$$

wherein $R^4$ is azido or a group of the sub-formula (a);

(b) a compound of the formula (V):

$$R^5O.CO.N=N.CO.OR^6 \quad (V)$$

wherein $R^5$ and $R^6$ are independently $C_{1-6}$ alkyl, aryl-$C_{1-6}$ alkyl or aryl; and (c) a compound of the formula (VI):

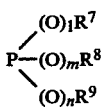 (VI)

wherein l, m and n are independently zero or one and $R^7$, $R^8$ and $R^9$ are independently $C_{1-6}$ alkyl, aryl $C_{1-6}$ alkyl or aryl and thereafter if necessary:
(i) reducing a compound of the formula (II) wherein $R^1$ is azido to form a compound of the formula (II) wherein $R^1$ is amino; or
(ii) hydrolyzing a compound of the formula (II) wherein $R^1$ is a group of the sub-formula (a) to form a compound of the formula (II) wherein $R^1$ is hydroxy.

2. A process as claimed in claim 1 wherein the stereochemical configuration at C-8 in the compound of the formula (III) is S and the stereochemical configuration at C-8 in the compound of the formula (II) is R.

3. A process as claimed in claim 1 wherein the compound of the formula (IV) is hydrazoic acid or formic acid.

4. A process as claimed in claim 1 wherein the compound of the formula (V) is diethylazodicarboxylate.

5. A process as claimed in claim 1, wherein the compound of the formula (IV) is triphenylphosphine.

* * * * *